United States Patent [19]

Wagner et al.

[11] Patent Number: 5,652,314

[45] Date of Patent: Jul. 29, 1997

[54] SHAPE-SHIFTED MAGNESIUM ALKOXIDE COMPONENT FOR POLYMERIZING OLEFINS

[75] Inventors: Burkhard Eric Wagner, Highland Park, N.J.; Daniel Paul Zilker, Jr., Charleston, W. Va.; Robert James Jorgensen, Belle Mead, N.J.

[73] Assignee: Union Carbide Chemicals & Plastics Technology Corporation, Danbury, Conn.

[21] Appl. No.: 701,805

[22] Filed: Aug. 21, 1996

Related U.S. Application Data

[62] Division of Ser. No. 596,777, Feb. 2, 1996, which is a division of Ser. No. 447,921, May 23, 1995, Pat. No. 5,567,665, which is a continuation of Ser. No. 221,684, Mar. 31, 1994, abandoned.

[51] Int. Cl.[6] .................................................. C08F 4/656
[52] U.S. Cl. ..................... 526/97; 526/124.4; 526/124.5; 526/124.6; 526/125.8; 526/908
[58] Field of Search ................................. 526/97, 124.4, 526/124.5, 124.6, 125.8, 908

[56] References Cited

U.S. PATENT DOCUMENTS

| | | | |
|---|---|---|---|
| 4,540,679 | 9/1985 | Arzoumanidis et al. | 502/111 |
| 4,612,299 | 9/1986 | Arzoumanidis et al. | 502/104 |
| 4,728,705 | 3/1988 | Nestlerode et al. | 526/125 |
| 5,034,361 | 7/1991 | Job et al. | 502/9 |

FOREIGN PATENT DOCUMENTS 64-10529  2/1989  Japan.

OTHER PUBLICATIONS

Boor, Jr., John, *Ziegler–Natta Catalysts and Polymerizations*, Academic Press, New York, 1979, pp. 602–609.

*Primary Examiner*—Romulo H. Delmendo
*Attorney, Agent, or Firm*—A. S. Reiskind

[57] ABSTRACT

A process is provided for preparing a shape-shifted catalyst component comprising (1) contacting a dihydrocarbyloxide magnesium compound with carbon dioxide in the presence of a slurrying agent to form a slurry of a carboxylated dihydrocarbyloxide magnesium compound; (2) adding a filler to the slurry either before or after the carboxylation of step (1); (3) spray drying the slurry of step (2) to evaporate the slurrying agent and to produce solid particles of the carboxylated dihydrocarbyloxide magnesium compound incorporating the filler; and, optionally, (4) heating the solid particles to remove carbon dioxide to produce a shape-shifted dihydrocarbyloxide magnesium compound component. A catalyst system using the component and a polymerization process employing the catalyst system are also provided.

8 Claims, 1 Drawing Sheet

5,652,314

SHAPE-SHIFTED MAGNESIUM ALKOXIDE COMPONENT FOR POLYMERIZING OLEFINS

This application is a divisional application of application Ser. No. 08/595,777 filed Feb. 2, 1996, which was a divisional application of U.S. patent application Ser. No. 08/447,921 filed May 23, 1995, now U.S. Pat. No. 5,567,665, which was a continuation of U.S. patent application Ser. No. 08/221,684 filed Mar. 31, 1984, now abandoned.

FIELD OF THE INVENTION

This invention relates to a process for preparing a shape-shifted catalyst component from a magnesium alkoxide or aryloxide, a catalyst system containing the shape-shifted catalyst component, and a process for polymerizing olefins using the catalyst system. The polyolefins so prepared have improved morphological properties, such as more uniform particle size and shape, higher bulk density, and a lower amount of fines, by means of the catalyst system containing a structurally coherent solid shape-shifted catalyst support component having a uniform particle size and shape.

BACKGROUND OF THE INVENTION

By shape-shifted what is meant is that the catalyst support component of the present invention changes in external shape and in its internal physical structure without changing in its chemical composition.

Olefin polymerization catalysts comprising an organoaluminum compound and a transition metal compound reacted with a solid magnesium support component are well known in the art. Various magnesium compounds have been employed, including organomagnesium compounds, magnesium halides, magnesium hydrocarbyl oxides, magnesium hydroxide, magnesium hydroxychloride, and the like. It is also well known that the activity of such catalysts and their ability to produce stereoregular olefinic polymers can be enhanced by the addition of an electron donor (Lewis base) independently and/or incorporating it into the supported transition metal component. Such catalysts and processes are described, for example, in U.S. Pat. Nos. 4,414,132; 4,540,679; 4,612,299; and 4,728,705.

Polymer compositions prepared with catalysts derived from magnesium hydrocarbyl oxides, such as described in U.S. Pat. Nos. 4,329,253; 4,393,182; 4,400,302; and 4,414,132 are highly prized due to their advantageous material properties. However, improvements in the resin particle morphology would still be desirable. The catalyst particles tend to be fragile in nature and shatter during polymerization, especially in gas phase polymerization, and produce smaller particles which are irregular in size and shape. Since the polymer produced during polymerization essentially replicates the morphology of the catalyst, the polymers obtained are likewise irregular in size and shape. In addition, some catalysts and the polymers produced with such catalysts contain a relatively high level particles less than 125 μm in diameter, also known as fines, which may coat the walls of the reactor during polymerization and make continuous operation, particularly commercial operation, difficult to sustain.

The morphological disadvantages associated with catalysts derived from some magnesium hydrocarbyl oxides appear to be associated with the external structure of the magnesium starting material as well as with the polymeric, cross-linked internal structure which generates non-optimal internal cohesiveness of the growing catalyst/polymer particle. However, the magnesium hydrocarbyl oxide supports commonly employed in the prior art tend to be fairly intractable both physically and chemically, so that changes in exterior and interior morphology are not readily achieved.

An alternative series of supports, the magnesium hydrocarbyl carbonates, can be prepared from hydrocarbyl oxides. One solution to the problem thus has been to change the morphology and internal structure of the starting magnesium alkoxide composition by conversion to a magnesium hydrocarbyl carbonate composition via treatment of the magnesium alkoxide with carbon dioxide followed by precipitation (U.S. Pat. No. 4,540,679) or by spray drying (U.S. Pat. No. 4,728,705). However, while these compositions result in active polymerization catalysts, they still have some disadvantages. Regardless of the above-described treatment of the magnesium compounds to improve morphological properties, the polymers produced with these catalyst need not be totally identical to polymers produced using magnesium hydrocarbyl oxides. Minute differences in polymer composition are frequently readily detected during commercial extrusion of the polymer into the final product. From the point of view of morphology, these magnesium supports, furthermore, still do not lead to the desired morphology suitable for fluidized processes without further treatment. When the magnesium hydrocarbyl carbonate is precipitated, additional steps such as agglomeration or pre-polymerization of the catalyst are known to be required to achieve the desired particle size of the catalyst and to improve the internal cohesiveness of the resulting agglomerated particles. Spray drying of the magnesium hydrocarbyl carbonate composition is a promising step toward generating larger and more cohesive particles. However, the physical nature of the magnesium hydrocarbyl carbonates (glassy, oily materials) causes formation of unacceptably large amounts of hollow-shelled catalyst and broken fragments derived from such catalyst. On $TiCl_4$-treatment of the spray-dried support at elevated temperatures, the sudden release of carbon dioxide causes formation of weak, puffed particles, which in turn readily disintegrate during polymerization. Finally, residual titanium alkoxide trapped in the final particle causes a decrease in catalyst productivity.

Accordingly, a need exists for a catalyst having uniform size and reasonably round shape capable of producing more uniform polymer particles having a high bulk density and a reduced level of fines, and a special need exists for a catalyst with the above properties which also produces a polymer substantially the same as one produced from a magnesium hydrocarbyl oxide support of the prior art.

SUMMARY OF THE INVENTION

In accordance with the present invention, there is provided a process for preparing a structurally strengthened, shape-shifted catalyst component comprising: (1) contacting a dihydrocarbyloxide magnesium compound with carbon dioxide in the presence of a slurrying agent to form a slurry of a carboxylated dihydrocarbyloxide magnesium compound, (2) adding a filler to the slurry either before or after the carboxylation of step (1); (3) spray drying the slurry of step (2) to evaporate the slurrying agent and to produce solid particles of the carboxylated dihydrocarbyloxide magnesium compound incorporating the filler; and, optionally, (4) heating the solid particles to remove carbon dioxide to produce a shape-shifted dihydrocarbyloxide magnesium compound component.

In another embodiment of the invention there is provided a catalyst system comprising an organoaluminum compound, a selectivity control agent (or outside electron donor), and a structurally strengthened shape-shifted catalyst component.

Still another embodiment of the invention provides a process for polymerizing one or more alpha-olefins containing 2 to 8 carbon atoms, which process comprises reacting the alpha-olefins in the presence of the above-described catalyst system.

DETAILED DESCRIPTION OF THE INVENTION

Process for Preparing the Catalyst Component

Figure 1:
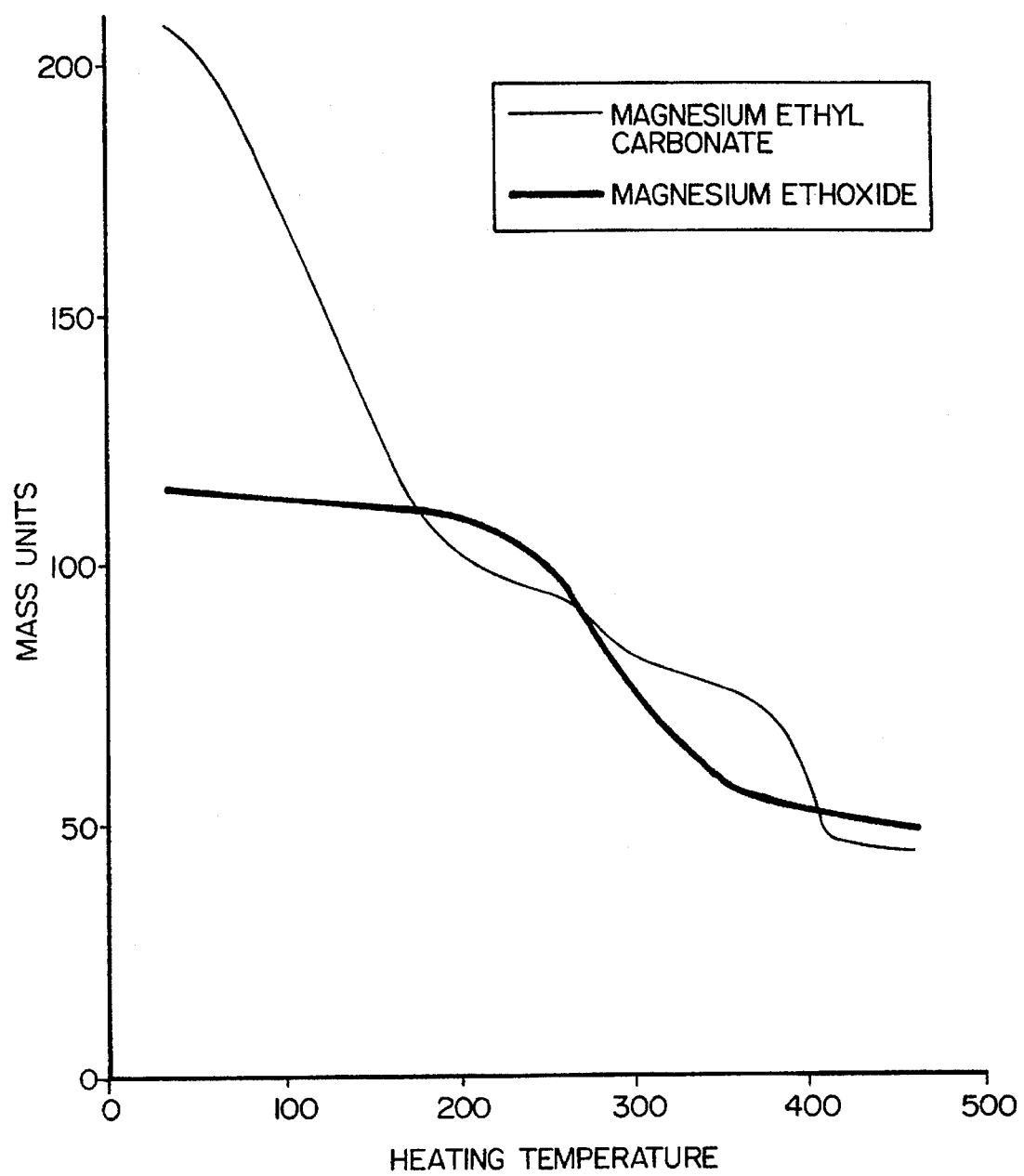
FIG. 1 is a graphic depiction of thermogravimetric analysis studies to more particularly illustrate heating temperatures for decarboxylation in the present invention.

The dihydrocarbyloxide magnesium compound employed in the preparation of the solid shape-shifted catalyst component can be represented by the formula:

$$Mg(OR)(OR')$$

wherein each of R and R' represent alkyl or aryl groups, which groups can be the same or different. Preferably the dihydrocarbyloxide magnesium compound employed is a magnesium dialkoxide or a magnesium diaryloxide, although magnesium compounds containing one alkoxide and one aryloxide group can also be employed. Most preferably, magnesium dialkoxides are employed. The alkoxide groups, when present, most suitably contain from 1 to 8 carbon atoms, preferably from 2 to 6 carbon atoms. The aryloxide groups, when present, most suitably contain from 6 to 10 carbon atoms.

Among the magnesium dialkoxides and diaryloxides which can be employed are magnesium diethoxide, magnesium diisopropoxide, magnesium di-n-butoxide, ethoxy magnesium isobutoxide, magnesium diphenoxide, and magnesium dinaphthoxide. Magnesium diethoxide is particularly preferred.

Illustrative of magnesium compounds containing one alkoxide and one aryloxide group which can be employed are ethoxy magnesium phenoxide and naphthoxy magnesium isoamyloxide.

The magnesium dialkoxides and diaryloxides are commercially available and can be used directly, as is, in the preparation of the shape-shined catalyst component. Alternatively, they can be prepared in-situ using magnesium metal and an alcohol wherein the alkoxide group of the alcohol and the alkoxide groups of the magnesium compound are the same.

The dihydrocarbyloxide magnesium compound is contacted with carbon dioxide. Carboxylation of the dihydrocarbyloxide magnesium compound is effected by suspending the dihydrocarbyloxide magnesium compound and optionally the filler in a suitable slurrying agent and contacting the slurry with carbon dioxide. The slurrying agent employed must be capable of at least partially dissolving the carboxylated dihydrocarbyloxide magnesium compound produced by the reaction. A monohydric alcohol is usually employed for this purpose, but other polar solvents such as acetone, dimethyl formamide or tetrahydrofuran (THF) are also suitable. If an alcohol is used, such alcohol preferably contains from 1 to 8 carbon atoms; and, in order to prevent undesirable transesterification reactions from occurring, it is desirable to employ an alcohol having a hydrocarbyloxy group which is the same as the hydrocarbyloxy groups of the magnesium compound. Ordinarily, an alcohol and a magnesium dialkoxide are employed wherein the alkoxide group of the alcohol and the alkoxide groups of the magnesium compound are identical. Most preferably the magnesium compound is magnesium ethoxide and the alcohol is ethanol. Other suitable alcohols include methanol, isopropanol, hexanol and their like.

Carboxylation of the dihydrocarbyloxide magnesium compound can be effected by simply bubbling gaseous carbon dioxide through the slurry of the dihydrocarbyloxide magnesium compound and optionally the flier in an alcohol or other polar slurrying agent. Alternatively, dry ice may be added to the slurry as the source of the carbon dioxide. Whatever the source of the carbon dioxide, it should be essentially anhydrous in order to avoid hydrolyzing the dihydrocarbyloxide magnesium compound. Continuous stirring of the slurry while the carbon dioxide is added is desirable in order to bring the carbon dioxide and the dihydrocarbyloxide magnesium compound into contact with each other and to prevent the dihydrocarbyloxide magnesium compound from settling out of the slurry.

Since the reaction between the carbon dioxide and the dihydrocarbyloxide magnesium compound is exothermic, the temperature of the mixture begins to rise as the carbon dioxide is added to the slurry. As the slurry warms and the reaction progresses, a turbid, viscous solution forms. If desired, addition of the carbon dioxide can be continued until the reaction has gone to completion as shown by the ending of the exotherm. In any event, reaction should be allowed to continue until a magnesium hydrocarbyl carbonate containing from 0.1 moles to 2.0 moles of carbon dioxide per gram atom of magnesium is produced. The magnesium hydrocarbyl carbonate produced in this manner can be represented by the formula:

$$Mg(OR)(OR') \bullet xCO_2$$

wherein each of R and R' represent alkyl or aryl groups, and x has a value of from 0.1 to 2.0. This material is believed to be made up of a mixture of two, and possibly more, components. These components include a mono-carboxylated component $$(ROMgOCOR')$$
$$\parallel$$
$$O$$

and a di-carboxylated component $$(ROCOMgOCOR').$$
$$\parallel \quad \parallel$$
$$O \quad O$$

If the filler has not been added before the carboxylation step, it should be added after. Any solid, inorganic, substantially non-porous particulate material can be employed as filler for the slurry provided that it is inert to the dihydrocarbyl oxide magnesium, the hydrocarbyl carbonate, and the slurrying agent and remains inert during subsequent spray drying and decarboxylation of the spray dried particles, as well as during preparation of the solid catalyst component from the decarboxylated particles and subsequent polymerization with such catalyst component. Suitable fillers include fumed silica, titanium dioxide, and calcium carbonate. Fumed hydrophobic silica is preferred because it imparts high viscosity to the slurry and does not chemically react with other components in the catalyst system. The particulate material employed as filler should have an average particle size no greater than 10 μm, preferably no greater than 0.1 to 1 μm. Such material should also be free of absorbed water. Optionally, when silica is employed it can be chemically treated to passivate surface hydroxyl groups.

Sufficient filler should be admixed with the solution of magnesium hydrocarbyl carbonate and slurrying agent to produce a slurry containing from about 10 weight percent to about 40 weight percent of the magnesium hydrocarbyl carbonate and from about 2 weight percent to about 10 weight percent of the flier. Preferably, sufficient filler is admixed with the slurry such that the slurry contains from about 15 weight percent to about 25 weight percent of the magnesium hydrocarbyl carbonate and from about 3 weight percent to about 8 weight percent of the filler.

The slurry comprising the carboxylated dihydrocarbyloxide magnesium compound, the filler, and the slurrying agent is spray dried. Spray drying may be effected by atomizing the slurry by means of a suitable atomizing device. Atomization is effected by passing the slurry through the atomizer together with an inert drying gas, i.e., a gas such as nitrogen or argon which is nonreactive under the conditions employed during atomization. An atomizing nozzle or a centrifugal high speed disc can be employed to effect atomization. The volumetric flow of drying gas must considerably exceed the volumetric flow of the slurry to effect atomization of the slurry and removal of excess slurrying agent. Optionally, the drying gas is heated to a temperature greater than the boiling point of the slurrying agent in which the magnesium hydrocarbyl carbonate is dissolved to as high as about 160° C. to facilitate atomization of the slurry and removal of the solvent. However, if the volumetric flow of drying gas is maintained at a very high level, it is possible to employ temperatures below the boiling point of the slurrying agent. If desired, the slurry may be pre-heated to a temperature as high as the boiling point of the slurrying agent before it is admixed with the drying gas. Atomization pressures of from about 1 psig to about 200 psig are suitable.

Surprisingly, the addition of a filler to the slurry before spray-drying results in the formation of discrete solid spray dried particles which while still raisin-like in appearance, are nevertheless full, cohesive, and mostly free of hollow shells and broken shells. It appears that the addition of filler has improved the cohesiveness of liquid droplets, thus allowing them to resist the deforming shear forces exerted on them during spray drying. The presence of a filler also provides voids in the framework of the sprayed particles which act as passageways through which solvent present therein can escape during the spray drying operation. This minimizes the formation of hollow particles which are easily shattered during spray drying. Use of shattered spheres would cause the introduction of irregularly shaped particles into the catalyst system and ultimately, of course, into the polymer produced with such system.

Spray drying produces discrete, substantially round, abrasive-resistant particles with relatively narrow particle size distribution. By adjusting the size of the orifices of the atomizer employed during spray drying, one obtains particles having an average particle size of from about 5 μm to about 200 μm, preferably from about 10 μm to about 30 μm. Filler is present in the spray dried particles in an amount of from about 10 weight percent to about 40 weight percent, preferably from about 15 weight percent to about 30 weight percent.

The discrete, full and round particles recovered from the spray drying step are then optionally decarboxylated by heating the particles at a temperature of from about 100° C. to 300° C. while purging carbon dioxide from the reaction vessel. Purging is preferably conducted using dry nitrogen gas.

Scale-up of the decarboxylation reaction in the absence of filler, such as described in U.S. Pat. No. 4,728,705, proved problematical beyond the bench level. Since the original carboxylation reaction was quite exothermic, higher temperatures must be employed for decarboxylation, and evolved carbon dioxide must be swept out quickly in order to prevent recarboxylation of magnesium sites. Heating at a higher temperature increases the rate of decarboxylation. But, Thermogravimetric Analysis (TGA) studies demonstrated that the effective temperatures for decarboxylation overlap the temperature range at which the first hydrocarbyl oxide moiety is lost from the resulting dihydrocarbyl oxide composition. There is, thus, an upper limit for the temperatures that can be employed, depending on the structure of the magnesium hydrocarbyl oxide. This phenomenon is graphically illustrated in FIG. 1. Heating at a too low but thermodynamically safe temperature results in unacceptably slow decarboxylation rates. There also is a limit on the permissible purge rate. The rate at which the evolved carbon dioxide can be swept out is limited by the velocity of the gas stream at which particles would be swept away. In consequence, one needs to use a longer decarboxylation time at lower reaction temperature using a limited purge gas velocity, which leads to a very limited reaction throughput.

In the present invention, it is theorized that the presence of filler in the particles facilitates their decarboxylation and allows the magnesium hydrocarbyl carbonate present to be reconverted to dihydrocarbyloxide magnesium with minimal subsequent decomposition. Surface area and porosity studies have shown that the filler provides voids in the framework of the particles which act as passageways which permit the carbon dioxide produced to escape from the interior of the particles. It is theorized that this both enhances the rate of removal of carbon dioxide and reduces the ability of the carbon dioxide to recombine with the decarboxylated product. At the same time, the presence of filler retards or precludes the flow of glassy magnesium hydrocarbyl carbonate which would reseal the generated voids, which would hinder further escape of carbon dioxide from the particles.

A temperature in excess of 300° C. should be avoided in order to prevent total thermal decomposition of the dihydrocarbyloxide magnesium. Preferably, the particles are decarboxylated at a temperature ranging from about 150° C. to about 275° C. To prevent the particles from agglomerating during decarboxylation, the particles should be agitated while heated to allow for adequate heat transfer, e.g., by means of a fluidized bed or a rotary kiln. If desired, heating may be conducted in a high boiling inert slurrying agent, i.e., one which is nonreactive with the particles and has a boiling point higher than that at which the particles are heated. Suitable slurrying agents include, e.g., isooctane, chlorobenzene and dodecane. When a slurrying agent is used, microporosity can be introduced such that the surface area of the shape-shifted magnesium dihydrocarbyl oxide can reach 200 m$^2$/g, compared to the 1 to 5 m$^2$/g found for either the starting magnesium dihydrocarbyl oxide or the filled magnesium dihydrocarbyl carbonate composition.

In order to prevent potential damage to the structure of the particles which may result from the rapid release of carbon dioxide when the particles are subsequently halogenated with the halogenated tetravalent titanium compound, heating should be continued for a period of time sufficient to fully decarboxylate the particles. Complete decarboxylation of the particles also ensures complete removal of any lingering solvent not fully removed during the spray drying step, which if allowed to remain in the particles can react with the halogenated tetravalent titanium compound to form undesirable by-products.

The particles produced by the decarboxylation retain the size and shape of the spray dried particles from which they are produced, as well as the structural integrity and abrasion resistance of the precursor particles. The structure of the particles does not appear to have suffered any obvious damage as a result of the decarboxylation.

Thus, by the successive steps of carboxylation, addition of filler, spray drying and decarboxylation, structurally coherent and abrasion resistant particles containing dihydrocarbyloxide magnesium are produced which have a more advantageous particle size, are substantially rounder and more uniformly sized than the irregularly-shaped particles of dihydrocarbyloxide magnesium used in their preparation. Especially noteworthy is the disappearance of the layered, polymeric magnesium alkoxide network structure in the interior of the particles, as shown by the crisp, two-stage decomposition pattern in the TGA of the shape-shifted dihydrocarbyloxide composition, compared to the broad, ill-defined single step decomposition pattern of the original magnesium dihydrocarbyloxide. The shape-shifted magnesium dihydrocarbyloxide plus filler composition appears to be much less cross-linked and more isotropic in structure, leading to a more cohesive catalyst and polymer particle.

The shape-shifted catalyst component generally contains dihydrocarbyloxide magnesium in an amount ranging from 60 weight percent to 90 weight percent and filler in an amount ranging from 10 weight percent to 40 weight percent. Preferably, the decarboxylated particles contain dihydrocarbyloxide magnesium in an amount ranging from 70 weight percent to 80 weight percent and filler in an amount ranging from 20 weight percent to 30 weight percent.

Catalyst System

The shape-shifted catalyst component of filler and dihydrocarbyloxide is then treated with a halogenated tetravalent titanium compound in the presence of an electron donor in order to halogenate the dihydrocarbyloxide magnesium present in the particles and to generate the solid component of the catalyst system, the procatalyst, which generally has the chemical composition $MgCl_2/TiCl_4/ED$ (ED=internal electron donor).

The halogenated tetravalent titanium compound employed to halogenate the dihydrocarbyloxide magnesium present in the particles must contain at least two halogen atoms, and preferably contains four halogen atoms. Most preferably these halogen atoms are chlorine atoms. However, titanium compounds containing up to two alkoxy and/or aryloxy groups can also be employed. The alkoxy groups, when present, most suitably contain from 1 to 8 carbon atoms, preferably from 2 to 6 carbon atoms. The aryloxy groups, when present, most suitably contain from 6 to 12 carbon atoms, preferably from 6 to 10 carbon atoms. Examples of suitable alkoxy- and aryloxy- titanium halides include diethoxy titanium dibromide, isopropoxy titanium triiodide, dihexoxy titanium dichloride, and phenoxy titanium trichloride.

Treatment of the decarboxylated particles with the halogenated tetravalent titanium compound, as noted, is conducted in the presence of an electron donor and, optionally in the presence of an aromatic, aliphatic or halohydrocarbon solvent. Preferably, the solvent is a halohydrocarbon, which can be aromatic, aliphatic, or alicyclic.

Aromatic halohydrocarbons are preferred, particularly those containing from 6 to 12 carbon atoms, and especially those containing from 6 to 10 carbon atoms. Preferably, such halohydrocarbons contain 1 or 2 halogen atoms, although more may be present if desired. Most preferably the halogen is present as chlorine. Suitable aromatic halohydrocarbons include chlorobenzene, bromobenzene, dichlorobenzene, dichlorodibromobenzene, chlorotoluene, dichlorotoluene, chloronaphthalene, and the like. Chlorobenzene and dichlorobenzene are preferred, especially the former.

The aliphatic halohydrocarbons which can be employed suitably contain from 1 to 12 carbon atoms. Preferably, such halohydrocarbons contain from 1 to 9 carbon atoms and at least 2 halogen atoms. Most preferably the halogen is present as chlorine. Suitable aliphatic halohydrocarbons include dibromomethane, trichloromethane, 1,2-dichloroethane, trichloroethane, dichlorofluoroethane, hexachloroethane, trichloropropane, chlorobutane, clichlorobutane, chloropentane, trichlorofluorooctane, tetrachloroisooctane, dibromodifluorodecane, and the like. Carbon tetrachloride and trichloroethane are preferred.

The alicyclic halohydrocarbons which can be employed suitably contain from 3 to 12 carbon atoms. Preferably such halohydrocarbons contain from 3 to 9 carbon atoms and at least 2 halogen atoms. Most preferably the halogen is present as chlorine. Suitable alicyclic halohydrocarbons include dibromocyclobutane and trichlorocyclohexane.

The aromatic hydrocarbons which can be employed are compounds such as toluene, xylene, ethyl benzene and the like. The aliphatic hydrocarbons are preferably high boiling hydrocarbons such as octane, isooctane, decane, dodecane, kerosene and the like. Preferred aromatic solvents are xylene and ethyl benzene. Preferred aliphatic hydrocarbon solvents are decane and dodecane.

The electron donor present during treatment of the decarboxylated particles with the halogenated tetravalent titanium compound is incorporated into the particles during such treatment and serves as an inside electron donor in the solid catalyst component prepared from the particles composed of titanium halide, magnesium halide, and electron donor. Suitable electron donors include organic compounds containing oxygen, nitrogen and/or phosphorus, such as ethers, esters, ketones, phenols, amines, amides, amides, imines, nitriles, phosphines, phosphine oxides, phosphites, phosphoramides, arsines and alcoholates. Examples of such electron donors can be found in U.S. Pat. No. 4,136,243 and British Specification No. 1,554,340.

Carboxylic acid esters are preferably employed as inside electron donors in the solid catalyst component and, therefore, are the electron donors preferably present during treatment of the decarboxylated particles with the halogenated tetravalent titanium compound.

Esters of monocarboxylic and dicarboxylic adds containing a total of from 2 to 32 carbon atoms are ordinarily employed. When a dicarboxylic add ester is employed, it is desirable for the two ester groups to be ortho to each other. Alkyl esters of aromatic carboxylic adds are preferred. Such esters usually contain a total of from 8 to 32 carbon atoms. Although alkyl esters of monocyclic aromatic acids are most preferred, esters of polycyclic aromatic adds can also be employed, as can esters of non-aromatic adds, including both aliphatic add and non-aromatic cyclic acids. When an alkyl ester of an aliphatic or non-aromatic cyclic add is employed, it is desirable for the aliphatic or non-aromatic cyclic group to contain at least one unsaturated bond. The non-aromatic cyclic group can be monocyclic or polycyclic. Esters of the non-aromatic cyclic acids usually contain a total of from 6 to 32 carbon atoms. If desired, the mono- or di- carboxylic add ester employed as inside electron donor can be substituted with one or more substituents which are inert under the reaction conditions employed during preparation of the solid catalyst component and polymerization with such catalyst component.

Examples of monocarboxylic and dicarboxylic acid esters which can be employed as inside electron donors include ethyl formate, ethyl acetate, ethyl acrylate, methyl methacrylate, ethyl propionate, i-propyl pivalate, methyl benzoate, ethyl benzoate, i-propyl benzoate, t-butyl benzoate, ethyl p-toluate, i-propyl p-toluate, n-amyl p-toluate, p-ethyl ethyl benzoate, p-methoxy ethyl benzoate, p-ethoxy methyl benzoate, p-ethoxy ethyl benzoate, p-chloro ethyl benzoate, p-amino n-hexyl benzoate, ethyl isopropyl oxalate, diethyl succinate, diisobutyl maleate, di-n-hexyl fumarate, diisoamyl citraconate, dimethyl adipate, dimethyl phthalate, diethyl phthalate, di-n-propyl phthalate, diisopropyl phthalate, di-n-butyl phthalate, diisobutyl phthalate, di-t-butyl phthalate, diisoamyl phthalate, di-t-amyl phthalate, dineopentyl phthalate, di-2-ethylhexyl phthalate, di-2-ethyldecyl phthalate, diethyl terephthalate, diethyl-1,2-fluorenedicarboxylate, cis-diisobutylcyclobutane-1,2-dicarboxylate, endo-diisobutyl-5-norbornene-2,3-dicarboxylate, and endo-diisobutyl-bicyclo [2.2.2] oct-5-ene-2,3-dicarboxylate, and the like.

Ethyl benzoate is the preferred monocarboxylic acid ester and diisobutyl phthalate is the preferred dicarboxylic acid ester.

Treatment of the shape-shifted catalyst component with the halogenated tetravalent titanium compound is effected employing an excess of the titanium compound. At least two moles of the titanium compound are ordinarily employed per gram atom of magnesium in the decarboxylated particles. Preferably from 4 moles to 100 moles of the titanium compound are employed per gram atom of magnesium in the decarboxylated particles, and most preferably from 4 moles to 20 moles of the titanium compound are employed per gram atom of magnesium in the decarboxylated particles.

Treatment the he shape-shifted catalyst component with the halogenated tetravalent titanium compound, as noted, is conducted, preferably in the presence of a halohydrocarbon and an electron donor. The halohydrocarbon is employed in an amount sufficient to dissolve the titanium compound and the electron donor, and to provide a dispersion of the solid, insoluble shape-shifted catalyst component in which halogenation of the dihydrocarbyloxide magnesium present in the shape-shifted component with the titanium compound can take place. Usually the halohydrocarbon is employed in an amount sufficient to provide a dispersion containing from 0.005 to 2.0 gram atoms of magnesium per mole of the halohydrocarbon, preferably from 0.01 to 1.0 gram atoms of magnesium per mole of the halohydrocarbon. The electron donor, which, as previously noted, serves as an inside electron donor in the solid catalyst component composed of titanium halide, magnesium halide and electron donor, is employed in an amount sufficient to provide a molar ratio of said compound to the titanium compound of from 0.0005:1 to 2.0:1, preferably of from 0.001:1 to 0.1:1.

Treatment of the shape-shifted catalyst component with the halogenated tetravalent titanium compound is effected at a temperature of from about 60° C. to about 150° C., preferably at a temperature of from about 70° C. to about 120° C. Usually treatment is conducted over a period of about 0.1 to 6 hours, preferably over a period of about 0.5 to 3.5 hours. For convenience, treatment is effected at atmospheric pressure, although higher and lower pressures can be employed if desired. When treatment has been concluded, the treated particles can be isolated from the liquid reaction medium by filtration, decantation or other suitable method.

After the resulting particles have been separated from the liquid reaction medium, they are treated one or more times with additional halogenated tetravalent titanium compound to assure substantially complete halogenation of the shape-shifted catalyst component present. This additional treatment removes residual alkoxy and/or aryloxy groups and maximizes catalyst activity. Preferably, the resulting particles are treated at least twice with separate portions of the halogenated tetravalent titanium compound. As in the initial treatment, at least 2 moles of the titanium compound are ordinarily employed per gram atom of magnesium in the particles, and preferably from 4 moles to 100 moles of the titanium compound are employed per gram atom of magnesium in the particles, most preferably from 4 moles to 20 moles of the titanium compound per gram atom of magnesium in the resulting particles.

Generally, the reaction conditions employed to treat the particles with additional titanium compound are the same as those employed during the initial treatment, although it is not necessary for the electron donor to be present during any subsequent treatment. The halohydrocarbon is usually employed, however, to dissolve the titanium compound and disperse the particles. Usually the dispersion contains from 0.005 to 2.0 gram atoms of magnesium per mole of halohydrocarbon, preferably from 0.01 to 1.0 gram atoms of magnesium per mole of halohydrocarbon.

After the particles have been treated one or more times with additional halogenated tetravalent titanium compound, they are separated from the liquid reaction medium, washed with an inert hydrocarbon to remove unreacted titanium compounds, and dried. The final product suitably has a titanium content of from 0.5 percent by weight to 6.0 percent by weight, preferably from 2.0 percent by weight to 4.0 percent by weight. The atomic ratio of titanium to magnesium in the final product is suitably between 0.01:1 and 0.2:1, preferably between 0.02:1 and 0.1:1. The electron donor is present in a ratio of electron donor to magnesium of from 0.005:1 to 10.0:1, preferably from 0.02:1 to 2.0:1.

The particles produced in the manner are substantially round, uniformly sized, and have a narrow particle size distribution. Although highly microporous, they are structurally coherent and abrasion resistant. The morphology of this catalyst component replicates the morphology of the shape-shifted magnesium hydrocarbyloxide component. Ordinarily such particles have an average particle size of from 5 to 50 μm and contain less than 5 percent of particles having a particle size of less than 1 μm. When these procatalyst particles are combined with an organoaluminum compound, as cocatalyst, and a selectivity control agent (or outside electron donor), a highly active catalyst system is formed which is capable of, for example, polymerizing olefins to produce stereoregular polymers having a narrow particle size distribution, high bulk density, and a low proportion of fines.

The organoaluminum compound employed as cocatalyst may be any of the known activators of olefin polymerization systems which employ a titanium halide. Trialkylaluminum compounds, are preferred, particularly those wherein each of the alkyl groups contain from 1 to 6 carbon atoms. Suitable organoaluminum cocatalysts include compounds having the formula:

$$Al(R^3)_d X_e H_f$$

wherein:
X is Cl or $OR^4$;
$R^3$ and $R^4$ are saturated hydrocarbon radicals containing from 1 to 14 carbon atoms, which radicals may be the same or different;

d is 1 to 3;
e is 0 to 2;
f is 0 or 1; and
d+e+f is equal to 3.

$R^3$ and $R^4$ may be substituted with one or more substituents which are inert under the reaction conditions employed during polymerization. Preferably $R^3$ and $R^4$ are alkyl radicals containing from 1 to 8 carbon atoms.

Such activator compounds can be employed individually or in combination thereof and include compounds such as $Al(CH_3)_3$, $Al(C_2H_5)_3$, $Al(C_2H_5)_2Cl$, $Al_2(C_2H_5)_3Cl_3$, $AlC_2H_5)_2H$, $Al(C_2H_5)_2(OC_2H_5)$, $Al(i-C_4H_9)_3$, $Al(i-C_4H_9)_2H$, $Al(C_6H_{13})_3$ and $Al(C_8H_{17})_3$.

In addition to the procatalyst and an aluminum alkyl, selectivity control agents are added during the polymerization to control polymer microstructure. Suitable selectivity control agents are esters and organic silicon compounds. Preferred esters are esters of aromatic carboxylic acids, such as ethyl and methyl benzoate, p-methoxy ethyl benzoate, p-ethoxy methyl benzoate, p-ethoxy ethyl benzoate, ethyl acrylate, methyl methacrylate, ethyl acetate, dimethyl carbonate, dimethyl adipate, dihexyl fumerate, dibutyl maleate, ethylisopropyl oxalate, p-chloro ethyl benzoate, p-amine hexyl benzoate, isopropyl naphthenate, n-amyl toluate, ethyl cyclohexanoate, propyl pivalate.

Any of the compounds suitable as an inside electron donor in the solid catalyst component may also be employed in the catalyst system as a selectivity control agent (outside or external electron donor); however, the electron donor employed as selectivity control agent will ordinarily differ from the electron donor employed as inside electron donor. If a monocarboxylic acid ester is employed as inside electron donor, it is preferred to also employ a monocarboxylic acid ester as selectivity control agent, albeit a different one than the one selected as inside electron donor. If a dicarboxylic acid ester is employed as inside electron donor, however, it is preferred to employ a silicon compound containing a silicon-oxygen-carbon linkage, such as discussed above, as selectivity control agent.

Silicon compounds containing at least one silicon-oxygen-carbon linkage are also useful as selectivity control agents. Suitable silicon compounds include compounds having the formula:

$$R^1{}_m SiY_n X_p$$

wherein:
Y is —$OR^2$ or —$OCOR^2$
each $R^1$ and $R^2$ is a hydrocarbon or cycloaliphatic radical containing from 1 to 20 carbon atoms;
X is hydrogen or halogen;
m is an integer having a value of from 0 to 3;
n is an integer having a value of from 1 to 4;
p is an integer having a value of from 0 to 1; and
m+n+V is equal to 4.

Each of $R^1$ and $R^2$ may be the same or different, and, if desired, substituted with one or more substituents which are inert under the reaction conditions employed during preparation of the solid catalyst component and polymerization with such catalyst component. Preferably $R^1$ and $R^2$ contain from 1 to 10 carbon atoms when they are aliphatic or alicyclic, and from 6 to 10 carbon atoms when they are aromatic.

Silicon compounds in which two or more silicon compounds are linked to each other by an oxygen atom may also be employed, provided the requisite silicon-oxygen-carbon linkage is also present.

Examples of silicon-containing compounds which can be employed include tetramethoxysilane, methyltrimethoxysilane, dimethyldimethoxysilane, trimethylmethoxysilane, diisobutyldimethoxysilane, n-propyltrimethoxysilane, dicyclohexyldimethoxysilane, cyclohexylisobutyldimethoxysilane, dicyclopentyldimethoxysilane, diphenyldimethoxysilane, tetraethoxysilane, dimethyldiethoxysilane, diethyldiethoxysilane, phenyltriethoxysilane, diphenyldiethoxysilane, and triphenylethoxysilane.

Ethyl benzoate and diisobutyl phthalate are the preferred inside electron donors. When ethyl benzoate is employed as inside electron donor, p-ethoxy ethyl benzoate is preferably employed as selectivity control agent. When diisobutyl phthalate is employed as inside electron donor, diisobutyldimethoxysilane, n-propyltrimethoxysilane, dicyclohexyldimethoxysilane, cyclohexylisobutyldimethoxysilane, dicyclopentyldimethoxysilane are preferably employed as selectivity control agent.

Polymerization Process

Polymerization is effected with the catalyst system of the present invention by contacting an alpha-olefin having 2 to 8 carbon atoms with a catalytically effective mount of the three components of the catalyst system, i.e., the solid catalyst component, cocatalyst and selectivity control agent. Polymerization can be effected continuously or in bulk, employing solution, slurry or gas phase techniques. Preferably, polymerization is effected in gas phase in a fluidized bed. Suitable fluid bed reaction systems useful for gas phase polymerizations are described, e.g., in U.S. Pat. Nos. 4,302,565, 4,302,566 and 4,303,771.

The three components of the catalyst system are usually introduced into the reactor through separate feed lines in order to more effectively control the amount of each of these materials in the reactor. However, if desired, two or all of the components may be partially or completely mixed with each other before they are introduced into the reactor. In either event, the cocatalyst and the selectivity control agent are employed in such amounts as to provide a molar ratio of cocatalyst to selectivity control agent of from 0.5:1 to 100:1, preferably from 2:1 to 50:1, and the cocatalyst and the solid catalyst component are employed in such amounts as to provide an atomic ratio of aluminum in the cocatalyst to titanium in the solid catalyst component of from 5:1 to 300:1, preferably from 10:1 to 200:1.

Both the cocatalyst and the selectivity control agent may be introduced into the reactor dissolved in an inert liquid solvent, i.e., a solvent which is nonreactive under the conditions employed during polymerization. Hydrocarbons such as isopentane, hexane, heptane, toluene, xylene, naphtha and mineral oil can be employed for this purpose. Generally, such solutions contain from 5 weight percent to 75 weight percent of the cocatalyst and/or the selectivity control agent. If desired, less concentrated or more concentrated solutions can be employed, or, alternatively, the cocatalyst and the selectivity control agent can be added in the absence of solvent, or, if desired, suspended in a stream of liquid monomer. When a solvent is employed and polymerization is conducted in gas phase, the amount of solvent introduced into the reactor should be carefully controlled so as to avoid the use of excessive quantities of liquid which would interfere with such polymerization.

The solvents employed to dissolve the cocatalyst and the selectivity control agent may also be employed to introduce the solid catalyst component into the reactor. Higher boiling solvents, such as mineral oil, are preferred for this purpose.

While the solid catalyst component may also be introduced into the reactor in the absence of solvent or suspended in liquid monomer, such solvents may be employed to disperse the solid catalyst component and facilitate its flow into the reactor. Such dispersions generally contain from 5 weight percent to 75 weight percent of the solid component.

The catalyst system of the present invention may be employed to polymerize alpha-olefins containing 2 to 8 carbon atoms per molecule. These alpha-olefins should not contain any branching closer than two carbon atoms removed from the double bond. Suitable alpha-olefins include ethylene, propylene, butene-1, pentene-1, hexene-1, 4-methyl-pentene-1, heptene-1 and octene-1. The preferred alpha-olefin is propylene.

The alpha-olefins employed in the process of the present invention may, if desired, be copolyermized with up to 20 mole percent of ethylene and/or another alpha-olefin containing 2 to 8 carbon atoms per molecule. Such copolymerizations are particularly useful in processes which employ sequential polymerization cycles to produce polymers having improved impact properties, e.g., by homopolymerizing an alpha-olefin in one reactor and subsequently copolymerizing it in a second reactor in the presence of the product of the first reactor. This technique has been employed to produce high impact polypropylene by a multi-stage process wherein propylene is homopolymerized in one reaction zone and then copolymerized with ethylene in a second reaction zone, arranged in sequence with the first reaction zone, in the presence of the homopolymer produced in the first reaction zone. When multiple reactors are employed in this manner, it is sometimes necessary to add additional cocatalyst to the second reactor in order to maintain an active catalyst. Additional amounts of the solid catalyst component and selectivity control agent are generally not required.

The temperature employed during polymerization can vary from about 10° C. to about 115° C. when polymerization is effected in gas phase or in a slurry, and from about 150° C. to about 250° C. when polymerization is effected in solution. When polymerization is conducted in gas phase, the temperature, of course, must be maintained below the sintering temperature of the polymer produced in order to prevent polymer agglomeration. On the other hand, the temperature employed during gas phase polymerizations must be sufficiently elevated to prevent substantial condensation of the reaction mixture to the liquid state, as such condensation will cause the polymer particles being produced to cohere to each other and likewise aggravate the polymer agglomeration problem. This difficulty is normally associated with the use of alpha-olefins having 5 or more carbon atoms which have relatively high dew points. While some minor condensation is tolerable, anything beyond this will cause reactor fouling.

The pressure employed can vary from subatmospheric to superatmospheric. Pressures of up to about 7000 kPa, preferably of from about 70 kPa to about 3500 kPa, are suitable for gas phase, slurry and solution polymerizations.

If desired, polymerization may be conducted in the presence of an inert gas, i.e., a gas which is nonreactive under the conditions employed during polymerization. A chain transfer agent, such as hydrogen, may also be present. The reactor should, however, be maintained substantially free of undesirable catalyst poisons, such as moisture, oxygen, carbon monoxide, carbon dioxide, acetylene, and the like.

When polymerization is conducted in a fluid bed, the superficial gas velocity of the gaseous reaction mixture through the bed must exceed the minimum flow required for fluidization in order to maintain a viable fluidized bed.

The polymers produced in accordance with the process of the present invention are granular materials having an average particle size of from about 0.01 to about 0.20 centimeters, usually of from about 0.02 to about 0.13 centimeters, in diameter.

The polymers produced in accordance with the process of the present invention have a bulk density of from about 200 kilograms per cubic meter to about 513 kilograms per cubic meter.

EXPERIMENTAL

The following Examples are designed to illustrate the present invention and are not intended as a limitation upon the scope thereof.

The properties of the polymers produced in the Examples were determined by the following test methods:

Melt Index (MI)

ASTM D-1238, Condition E. Measured at 230° C. and reported as grams per 10 minutes.

Productivity

A sample of the resin product is ashed, and the weight percent of ash is determined. The amount of Ti in the ash is determined spectrophotometrically. Productivity is expressed in terms of parts per million of Ti in the polymer.

Fines

Weight percent of polymer particles which pass through a 120 mesh U.S. Standard screen.

Average Resin Particle Size

Calculated from sieve analysis data according to ASTM D-1921, Method A, using a 500 g sample. Calculations are based on weight fractions retained on the screens.

Bulk Density

ASTM D-1895, Method B. The resin is poured via ⅜" diameter funnel into a 400 ml graduated cylinder to the 400 ml line without shaking the cylinder, and weighed by difference.

Support or Catalyst Particle Size

The term D10, D50 and D90 indicate particular percentiles of log normal particle size distribution determined by means of a Leeds and Northrup Micro-trac® particle size analyzer using a dodecane solvent. Thus, e.g., catalyst particles having a D50 of 12 μm have a median particle size of 12 μm. A D90 of 18 μm indicates that 90% of the particles have a particle size of less than 18 μm, and a D10 of 8 μm indicates that 10% of the particles have a particle size of less than 8 μm.

Xylene Solubles

A sample is weighed and completely dissolved in xylene in a flask by heating under reflux at 120° C. with stirring. The flask is then immersed in a water bath at 25° C. for one hour, during which time the insoluble polymer precipitates. The precipitate is filtered off, and the amount of soluble polymer present in the filtrate is determined by evaporating a 100 ml aliquot of the filtrate, drying the residue under vacuum, and weighing the residue. The xylene-soluble content consists of amorphous material with some low molecular weight crystalline material.

EXAMPLES

A. PREPARATION OF SHAPE-SHIFTED SUPPORT

Step I:

Carboxylation of Magnesium Ethoxide

Into a 1900 liter glass-lined reactor equipped with a turbine agitator were added 150 kilograms of magnesium ethoxide and 532 kilograms of ethanol under a nitrogen atmosphere (<10 ppmv $H_2O$). The contents of the reactor were continuously stirred at approximately 50 rpm while carbon dioxide was continuously bubbled through the mixture at a rate of approximately 20–25 kgs/hr until 116 kgs of carbon dioxide were fed. The reactor jacket temperature was maintained at ≈35° C. for the duration of the carboxylation reaction. The exotherm resulting from the addition of carbon dioxide caused the temperature of the mixture to rise to approximately 5°–10° C. over a period of about 60 minutes. Additional $CO_2$ was added to achieve the desired stoichiometry. At the end of this time, the magnesium ethoxide had completely dissolved in the ethanol forming a clear, viscous solution under $CO_2$ atmosphere. Excess $CO_2$ was vented and the mixture analyzed at 4.03 wt % magnesium. This mixture was used as a stock solution for further dilution and addition of inert filler.

Step II.

Examples 1–13

Spray Drying of Carboxylated Magnesium Ethoxide

Sufficient fumed silica having a particle size in the range of from 0.1 μm to 1 μm (CAB-O-SIL® TS-610, manufactured by the Cabot Corporation) was added to the solution prepared in accordance with (Step I) above. The mixture was stirred by means of a turbine agitator during this time and for several hours thereafter to thoroughly disperse the silica in the solution. The temperature of the mixture was held at 30° C. throughout this period and a nitrogen atmosphere (<5 ppm $H_2O$) was maintained at all times. Additional ethanol was added as needed to achieve the desired magnesium content of the feed.

The resulting slurry was spray dried using an 8-foot diameter closed cycle spray dryer equipped with a rotary atomizer. The rotary atomizer speed was adjusted to produce particles with a wide range of particle sizes. The scrubber section of the spray dryer was maintained at approximately −4° C.

Nitrogen gas was introduced into the spray dryer at inlet temperatures of 100°–140° C. and was circulated at a rate of approximately 1700 kg/hour. The fumed silica/carboxylated magnesium ethoxide slurry was fed to the spray dryer at a temperature of about 35° C. and a rate sufficient to yield an outlet gas temperature of approximately 70°–100° C. The atomization pressure was slightly above atmospheric.

The spray dried particles had a D10, D50 and D90 determined by means of a Leeds and Northrup Micro-trac® particle size analyzer using a dodecane solvent. Results are given in the Table 1 below. Spray dried particles were collected in two fractions, one fraction from the main drying chamber and the second fraction from the cyclone separator. In practice, the chamber fractions consists of larger particles. Note that some decarboxylation does occur at the temperature of spray drying due to the relatively high magnesium content of some of the samples. The decarboxylation, however is only partial under these conditions.

Step III:

Decarboxylation of Spray Dried Particles

Specific samples of the spray dried particles prepared in accordance with Examples 1 to 13 were heated in a rotary evaporator in quantities of ≈250 grams at a heating bath temperature of 150° C. for 24 hours under a vacuum (28 inch of mercury vacuum) with a nitrogen purge of 0.2 cc/gram support/minute to completely remove carbon dioxide and any remaining ethanol present. The particles underwent a weight loss of equivalent to removal of all carbon dioxide present. In addition, FTIR (Fourier Transform Infarred Spectroscopy) indicated no detectable carbonyl in any of the decarboxylated samples, indicating complete conversion to magnesium ethoxide. The decarboxylated particles retained the solid round shape and dimension of the original spray dried particles and did not appear to undergo any structural deterioration as a result of this treatment.

These particles are substantially rounder and more uniformly sized than the irregularly shaped particles of magnesium ethoxide used in their preparation.

Step IV:

Examples 14 to 16

Treatment of Shape-Shifted Support Particles with $TiCl_4$ and Electron Donor And Conversion to Procatalyst To a 11.5 liter working capacity reactor were added in the following order at room temperature while stirring at a rate sufficient to suspend the solids added under a dry nitrogen atmosphere (<10 vppm $H_2O$): chlorobenzene, titanium tetrachloride, the desired quantity of the solid support prepared in (c) above and an approximately 50 wt % solution of diisobutyl phthalate in chlorobenzene. It should be noted that the order of addition is not critical, however it is typically easier to ensure that all of the support is properly mixed if the dry solid is added to the solution of titanium tetrachloride and chlorobenzene. In a typical preparation, an amount of support containing 3.0 to 3.5 moles of contained magnesium (either as the shape-shifted ethoxide as prepared in Step III above or as the carboxylated magnesium ethoxide as produced in Step II above) is converted to pro-catalyst. Initial total charges are: chlorobenzene-4.7 liters, titanium tetrachloride-8.2 kilograms, 187 grams (180 milliliters, 0.67 Moles) of diisobutyl phthalate. These correspond to ≈0.33–0.35 millimoles of Mg/cc of solvent (i.e. the mixture of chlorobenzene and titanium tetrachloride) and a molar ratio of 0.13 moles of diisobutyl phthalate/mole of magnesium added to the reactor.

After addition of the above materials to the reactor, the temperature of the reactor is raised first to 50° C. and held for 30 minutes, then to 105°–110° C. and held for 60 minutes. The slurry is filtered. Solid round particles were collected. The solids were reslurried in a solvent mixture of titanium tetrachloride and chlorobenzene (≈8.2 kg of $TiCl_4$ and 4.7 liters of chlorobenzene). A quantity of phthaloyl dichloride equivalent to 0.049–0.05 moles/mole of magnesium in the starting support is added. The mixture is heated over a period of about 30 minutes up to 105°–110° C. and stirred for an additional 60 minutes.

The slurry is filtered as before. Solid round particles were collected. These particles were reslurried in an equivalent mixture of titanium tetrachloride and chlorobenzene with the exception that phthaloyl dichloride was not added. The mixture is heated to 105°–110° C. and stirred for an additional 10–30 minutes and filtered again. The solids are washed with 6 times with dry hydrocarbon solvent (hexane is typically used). Approximately 1500 milliliters of solvent is used in each wash. The solids are filtered after each wash to remove solvent and any residual titanium tetrachloride present. After the last wash is completed, the solid round particles are dried with a nitrogen flow and then placed into a mineral oil slurry (Kaydol®) of approximately 25–30 wt % solids.

The treated particles retained the round shape and the dimension of the original decarboxylated particles and did not appear to undergo any structural deterioration as a result of this treatment. Further details on the preparation are given in Table 2 along with analysis of the supports and the final catalysts.

B. Examples 17-19

POLYMERIZATION

The round catalyst particles prepared as described in Step IV, Examples 14 to 16, were employed together with triethylaluminum, as cocatalyst, and diisobutyldimethoxysilane, as selectivity control agent or outside electron donor, to polymerize propylene in a fluid bed reactor system similar to that described and illustrated in U.S. Pat. Nos. 4,302,565; 4,302,566; and 4,303,771.

The round catalyst particles were continually fed to the polymerization reactor as ≈30 percent dispersion in mineral oil. The triethylaluminum cocatalyst was employed as a 2.5 percent solution in isopentane, and the silane selectivity control agent was employed as a 1 percent solution in isopentane.

Hydrogen was added to the reactor as a chain transfer agent to regulate the molecular weight of the polymer produced. Nitrogen was added as a diluent gas.

The polymer particles obtained were quite round and contained a low proportion of fines.

Table 3 below summarizes the reaction conditions employed during polymerization, the properties of the polymers produced, and the productivity of the catalyst system.

Comparative Example A

Use of Commercial Magnesium Ethoxide

(A) CATALYST PREPARATION

A solid catalyst component was prepared as described in Step IV above except that 378 grams (3.3 moles) of commercial magnesium ethoxide obtained from Dynamit-Nobel was substituted for the decarboxylated spray dried particles prepared in accordance with Examples 1–13, Step III.

The catalyst particles obtained in this manner contained 2.7 weight percent Ti and 18.5 weight percent Mg.

(B) POLYMERIZATION

Comparative Examples A(1)–A(3)

For comparative purposes, propylene was polymerized as in Examples 17-19 above using the solid catalyst component prepared as above together with triethylaluminum, as cocatalyst, and diisobutyldimethoxysilane, as selectivity control agent or outside electron donor.

The polymer particles obtained were irregularly shaped compared to the polymer particles obtained in Examples 17-19. In addition, excessive amounts of fine particles were obtained as indicated in Table 3. In particular, the amount of fines in the <60 micron size range was very high at 6–12 wt %.

Comparative Example B

Use of Non-Decarboxylated Magnesium Ethyl Carbonate Produced without Filler

(A) CATALYST PREPARATION

A solid catalyst component was prepared as described in Step IV above. The solution of carboxylated magnesium ethoxide was spray dried. The particles collected as part of Example 6 and 12 (from Table 1) were converted into catalyst following the procedure described in Step IV above. Step III (Decarboxylation) was omitted. The particles did not flow readily, easily clumped up, and easily picked up and maintained an electrostatic charge. The carboxylated particles employed contained 5.2 moles of magnesium ethoxide.

Results are given in Table 2 as Comparative Examples B(1) and B(2).

(B) POLYMERIZATION

Comparative Examples B(1) and B(2)

For comparative purposes, propylene was polymerized as in Examples 17-19 above using the solid catalyst component prepared as above together with triethylaluminum, as cocatalyst, and diiisobutyldimethoxysilane, as selectivity control agent or outside electron donor.

The polymer particles obtained, while much rounder and considerably more uniform in size and shape than the polymer particles obtained in Comparative Example A (not spray dried), were not as low in fines as the polymer particles obtained in the presence of a filler (Examples 17–19).

The details of these polymerizations are set forth in Table 3.

In particular, compare polymerization results using the catalyst made from support produced in Example 6 (Table 1) (no filler, carboxylated) vs. polymerization results using catalyst made from support n-tuber 8 (with filler, decarboxylated). These two supports were produced using identical feed compositions except for the addition of filler and decarboxylation in the procatalyst produced using support from Example 8. Also, compare the difference in fines levels between Example 19 and Comparative Example B(1). In this case, there is a direct comparison between supports produced with and without filler. The addition of a filler in the support resulted in polymer with substantially reduced fines (2.4% for Example 19 vs. 4.6% in Comparative Example B(1)). Surprisingly, increasing the average size of the catalyst particle does not result in a reduction in fines unless a filler is included in the support. To illustrate this, compare polymerization results given in Example 17 to Comparative Example B(2). The support used in preparation of the catalyst for Example 17 had a D50 of 38 microns compared to 43 microns for the support used for Comparative Example B(2). Despite this large size, note that Comparative Example B(2) results in high fines (7.4% vs. <1% for the catalyst of the invention). In particular, the fines through the #200 mesh screen are lower in the catalysts of the invention due to the absence of broken shells attributable to fracture of the support during conversion to catalyst. It should be noted that fines in this range are particularly harmful to long term operability since they are typically rich in catalyst residues and are easily carried over into the cycle piping to cause fouling.

TABLE 1

Preparation of Shape-Shifted Catalyst Component Preparation of Spray Dried Support

| Example Number | 1 | 2 | 3 | 4 | 5 | 6 | 7 |
|---|---|---|---|---|---|---|---|
| Feed Composition | | | | | | | |
| Mg wt % | 3.9 | 3.9 | 3.9 | 3.9 | 3.9 | 2 | 2 |
| Total Solids wt % | 32.4 | 32.4 | 32.4 | 32.4 | 32.4 | 16.6 | 16.6 |
| Filler wt % | 0 | 0 | 0 | 0 | 0 | 0 | 0 |
| Drying Conditions | | | | | | | |
| Temperature | 70 | 65 | 60 | 70 | 70 | 60 | 60 |
| Atomizer Speed (rpm/1000) | 20 | 15 | 15 | 12 | 9 | 9 | 9 |
| Inlet Gas Temperature °C. | 121 | 120 | 121 | 120 | 121 | 120 | 120 |
| Outlet Gas Temperatrure °C. | 81 | 80 | 71 | 80 | 81 | 80 | 80 |
| Condenser Outlet Temperature °C. | 10 | 10 | 10 | 10 | 10 | 10 | 20 |
| Cycle Gas Flow rate kg/hr | 1015 | 1040 | 1040 | 1040 | 1040 | 1040 | 1040 |
| Product Analysis | | | | | | | |
| Product-Chamber | | | | | | | |
| Mg % wt | 13.47 | 14.03 | nd | nd | 13.43 | 14.24 | 13.22 |
| D90 Microns | 67 | 71 | 71 | 129 | 61 | 62 | 63 |
| D50 | 33 | 37 | 38 | 46 | 26 | 32 | 30 |
| D10 | 9 | 12 | 10 | 9 | 8 | 8 | 8 |
| Product-Cyclone | | | | | | | |
| Mg % wt | 16.96 | 16.76 | 16.85 | 18.08 | 14.55 | 15.3 | 15.25 |
| D90 Microns† | 50 | 50 | 49 | 49 | 61 | 46 | 46 |
| D50† | 24 | 24 | 22 | 24 | 27 | 21 | 20 |
| D10† | 8 | 8 | 8 | 8 | 8 | 7 | 7 |

| Example Number | 8 | 9 | 10 | 11 | 12 | 13 |
|---|---|---|---|---|---|---|
| Feed Composition | | | | | | |
| Mg wt % | 2 | 4 | 1.96 | 3.6 | 3.6 | 3.94 |
| Total Solids wt % | 20.2 | 33.4 | 23.3 | 36.9 | 29.9 | 32.8 |
| Filler wt % | 3.5 | 3.5 | 7 | 7 | 0 | 0 |
| Drying Conditions | | | | | | |
| Temperature | 55 | 70 | 74 | 70 | 75 | 70 |
| Atomizer Speed (rpm/1000) | 9 | 9 | 9 | 9 | 15 | 15 |
| Inlet Gas Temperature °C. | 120 | 120 | 120 | 120 | 100 | 139 |
| Outlet Gas Temperatrure °C. | 81 | 81 | 80 | 80 | 70 | 71 |
| Condenser Outlet Temperature °C. | 10 | 10 | 10 | 10 | 10 | 10 |
| Cycle Gas Flow rate kg/hr | 1040 | 1040 | 1040 | 1040 | 1040 | 1040 |
| Product Analysis | | | | | | |
| Product-Chamber | | | | | | |
| Mg % wt | 11.03 | 12.61 | 9.81 | 12.41 | 15.06 | nd |
| D90 Microns | 78 | 81 | 102 | 108 | 95 | 119 |
| D50 | 34 | 33 | 47 | 40 | 36 | 40 |
| D10 | 7 | 7 | 6 | 7 | 8 | 9 |
| Product-Cyclone | | | | | | |
| Mg % wt | 13.01 | 12.38 | 9.9 | 11.96 | 16.43 | 16.09 |
| D90 Microns† | 47 | 60 | 54 | 64 | 65 | 51 |
| D50† | 20 | 26 | 27 | 27 | 25 | 24 |
| D10† | 6 | 7 | 9 | 9 | 7 | 7 |

*nd = not determined
† diameter at 90, 50, 10 percent distribution, respectively.

TABLE 2

Preparation of Shape-Shifted Catalyst Component Conversion of Support into Procatalyst

| Example Number | Comp. Ex. A | 14 | 15 | Comp. Ex B(1) | 16 | Comp. Ex B(2) |
|---|---|---|---|---|---|---|
| Filler/No Filler | Comp. Ex. A | Filler | Filler | No Filler | Filler | No Filler |
| Filler (fumed silica from Cabot Corporation) | | TS-610 | TS-610 | | TS-610 | |
| Support from Example # | Mg(OEt)2 | 8-CH | 8-Cy | 6-Cy | 9-Cy | 12-Ch |
| Decarboxylated (Yes/No) | na | yes | yes | no | no | no |
| Magnesium wt %-Support | 21.3 | 16.27 | 16.23 | 15.3 | 12.4 | 15.1 |

TABLE 2-continued

Preparation of Shape-Shifted Catalyst Component Conversion of Support into Procatalyst

| Example Number | Comp. Ex. A | 14 | 15 | Comp. Ex B(1) | 16 | Comp. Ex B(2) |
|---|---|---|---|---|---|---|
| Phthalate/Mg Ratio | 0.13 | 0.13 | 0.13 | 0.223 | 0.13 | 0.13 |
| Phthaloyl Chloride/Mg | 0.049 | 0.046 | 0.049 | 0.036 | 0.049 | 0.049 |
| Slurry Conc. mmMg/cc | 0.4 | 0.35 | 0.35 | 0.33 | 0.35 | 0.35 |
| Catalyst Ti Content wt % | 2.7 | 1.37 | 1.36 | 2.33 | 1.71 | 1.37 |
| Catalyst Mg Content wt % |  | 15.14 | 15.2 | 12 | 14.1 | 18.6 |
| Support D50 | nd | 38 | 22 | 22 | 29 | 43 |
| Support D10 | nd | 7 | 6 | 6 | 7 | 7.5 |
| Support D90 | nd | 75 | 40 | 42 | 52 | 85 |

Notes: CH = Fraction of spray dried support collected from the chamber of the spray dryer
CY = Fraction of spray dried support collected from the cyclone of the spray dryer.
D 10, 50 and 90 are the percentiles < than as measured using a Leeds and Northrup Microtrak ®. All values are in microns
Supports were decarboxylated as in Example 1.
D stands for decarboxylated, N for not decarboxylated.
Note that the magnesium content is higher than theoretical. Some decarboxylation to the ½ carbonate occurs in the spray dryer.

TABLE 3

Polymerization Results of Shape-Shifted Procatalysts Effect of Filler on Shape Retention and Fines Reduction

| Example Number | Comp. Ex A | 17 | 18 | Comp. Ex. B(1) | 19 | Comp. Ex. B(2) | Comp. Ex A(2) | Comp. Ex. A(3) |
|---|---|---|---|---|---|---|---|---|
| Decarboxylated (yes/no) | NA | yes | yes | no | no | no | NA | NA |
| Filler or No Filler | NA | Filler | Filler | No Filler | Filler | No Filler | na | na |
| Support Number (Table 1) |  | 8 Chamber | 8 Cyclone | 6 cyclone | 9 Cyclone | 12 Chamber | Comp. Ex. | Comp. Ex. |
| CATALYST TYPE | Comp Ex. A |  |  |  |  |  |  |  |
| CATALYST EXAMPLE (Table 2) | Comp. Ex. A | 14 | 15 | Comp. Ex. B(1) | 16 | Comp. Ex. B(2) | Comp. Ex. A | Comp. Ex. A |
| Decarboxylated (yes/no) |  | yes | yes | no | no | no | Mg(OEt)2 | Mg(OEt)2 |
| POLYMERIZATION COND. |  |  |  |  |  |  |  |  |
| TEMPERATURE (C.) | 80 | 80 | 80 | 80 | 80 | 80 | 80 | 80 |
| TOTAL PRESSURE KPA | 3134 | 3134 | 3134 | 3134 | 3134 | 3134 | 3134 | 3134 |
| H2/C3 mole ratio | 0.0019 | 0.0019 | 0.0021 | 0.01 | 0.0017 | 0.0019 | 0.0014 | 0.0014 |
| C3H6 MOLE % | 89.18 | 84.1 | 84.5 | 87 | 84 | 84.5 | 86 | 86.3 |
| PRODUCTION RATE kg/hr | 17 | 14.3 | 16.4 | 10.5 | 15.7 | 21 | 20.1 | 17.6 |
| Bed wt Kg | 21.4 | 21.4 | 45.9 | 21.4 | 21.4 | 21.4 | 40 | 21.4 |
| ACT. RES. TIME | 1.25 | 1.492063 | 1.275 | 2.04 | 1.36 | 1.01 | 1.98 | 1.21 |
| COCATALYST | 2.5% TEA | 2.5% TEA | 2.5% TEA | 2.5% TEA | 2.5% TEA | 2.5% TEA | 2.5% TEA | 2.5% TEA |
| COCAT. FLOW (cc/hr) | 230 | 192 | 434 | 393 | 393 | 326 | 382 | 372 |
| SCA | 2% DIBDMS | 2% DIBDMS | 2% DIBDMS | 2% DIBDMS | 2% DIBDMS | 2% DIBDMS | 2% DIBDMS | 2% DIBDMS |
| SCA FLOW (cc/hr) | 273 | 265 | 620 | 143 | 104 | 241 | 166 | 118 |
| CARRIER FLOW | PROPYLENE | PROPYLENE | PROPYLENE | PROPYLENE | PROPYLENE | PROPYLENE | PROPYLENE | PROPYLENE |
| POLYMER PROPERTIES |  |  |  |  |  |  |  |  |
| MELT FLOW RATE, dg/min | 2.27 | 2.84 | 2.48 | 13.64 | 2.75 | 2.95 | 2.77 | 2.45 |
| BULK DENSITY g/cm3 | 0.37 | 0.367 | 0.375 | 0.433 | 0.41 | 0.4 | 0.435 | 0.42 |
| FLUIDIZED BULK DENSITY | NOT AVAIL | 0.166 | 0.155 | 0.146 | 0.16 | 0.15 | 0.147 | 0.096 |
| APS Micron | 419 | 891 | 600 | 638 | 716 | 478 | 531 | 384 |
| SCREEN WT % #10 (>2000μ) | 0.6 | 1.19 | 0 | 0.4 | 1.4 | 0.2 | 1.4 | 0.2 |
| SCREEN WT % #18 (>1000μ) | 7.8 | 34.19 | 8.58 | 16.8 | 19.4 | 6.39 | 14.6 | 6.83 |
| SCREEN WT % #35 (>500μ) | 22.2 | 46.12 | 49.7 | 38.2 | 42.8 | 29.14 | 26.2 | 23.29 |
| SCREEN WT % #60 (>250μ) | 19.2 | 13.12 | 32.14 | 26.4 | 23 | 39.12 | 15.4 | 16.87 |
| SCREEN WT % #120 (>125μ) | 28.2 | 4.37 | 8.18 | 13.6 | 11 | 17.76 | 14.2 | 17.47 |
| SCREEN WT % #200 (>60μ) | 16 | 0.99 | 1.2 | 3.8 | 2.2 | 6.19 | 19 | 23.29 |
| SCREEN WT % #PAN (<60μ) | 6 | 0 | 0.2 | 0.8 | 0.2 | 1.2 | 9.2 | 12.05 |
| FINES THU 120 MESH | 22 | 0.99 | 1.4 | 4.6 | 2.4 | 7.39 | 28.2 | 35.34 |
| ASH wt % | 0.006 | 0.015 | 0.025 | [0.013] | 0.024 | 0.015 | 0.015 | 0.017 |
| Ti (ppmw) | 1.97 | 1.4 | 1.95 | [1.04] | 0.83 | 1.19 | 1.15 | 1.55 |
| Al/SCA Mole Ratio | 1.87 | 1.62 | 1.549 | [5.79] | 8.47 | 3.03 | 5.16 | 7.1 |
| Al/Ti Mole Ratio | 48.9 | 70.3 | 100.7 | [105] | 207 | 81.16 | 107.2 | 94.9 |
| XYLENE SOLUBLES wt % | 1.65 | 2.1 | 1.87 | 1.38 | 2 | 2.12 | 2.4 | 2.4 |

NOTE: SCA stands for Selectivity Control Agent or External Electron Donor. TEA = Triethyl Aluminum contained in isopentane solvent. DIBDMS = Diisobutyl Dimethoxy silane, also in isopentane solvent. The carrier is used to introduce the catalyst slurry into the reactor.
4 hr AVERAGES: PRODUCTION RATE; 2 HR AVERAGES: COCAT. FLOW, SCA FLOW, Al/SCA, Al/Ti; 1 HR AVERAGE: Fluidized Bulk Density
6 Hour Average: Particle Size; 12 Hour Average, Settled Bulk DENSITY

What is claimed is:

1. A process for polymerizing one or more alpha-olefins having 2 to 8 carbon atoms, which process comprises reacting the alpha-olefins in the presence of the catalyst system comprising:

(a) an organoaluminum compound, (b) a selectivity control agent, (c) a catalyst component prepared by:

(1) contacting dihydrocarbyloxide magnesium with carbon dioxide in the presence of a slurrying agent to form a magnesium hydrocarbyl carbonate;

(2) adding a filler having an average particle size of no greater than 1 μm, either before or after the dihydrocarbyloxide magnesium is contacted with carbon dioxide;

(3) spray drying the slurry of step (2) to evaporate the slurrying agent and to produce solid particles of magnesium hydrocarbyl carbonate incorporating the filler;

(4) heating the solid particles to remove carbon dioxide to produce a dihydrocarbyloxide magnesium catalyst component having an average particle size from about 5 μm to 200 μm; and (5) treating the catalyst component of (4) with a halogenated tetravalent titanium compound in the presence of an electron donor.

2. A process according to claim 1 wherein the dihydrocarbyloxide magnesium compound is prepared in the slurry by reacting magnesium metal with an alcohol.

3. The process according to claim 2 wherein the filler is a substantially non-porous, inert material selected from the group consisting of fumed silica, titanium dioxide, and calcium carbonate.

4. The process according to claim 3 wherein in step (3) the solid particles are heated to a temperature ranging from about 100° C. to about 325° C.

5. The process according to claim 4 wherein the slurrying agent is a polar slurrying agent in which the magnesium hydrocarbyl carbonate is soluble.

6. The process according to claim 5 wherein the dihydrocarbyloxide magnesium compound is magnesium ethoxide.

7. A process according to claim 6 wherein the slurrying agent is ethanol and the filler is fumed silica.

8. A process according to claim 1 wherein at least one alpha-olefin is propylene.

* * * * *